(12) United States Patent
Tulchinsky et al.

(10) Patent No.: US 8,586,793 B2
(45) Date of Patent: Nov. 19, 2013

(54) PROCESS FOR THE REDUCTIVE AMINATION OF ALDEHYDES AND KETONES VIA THE FORMATION OF MACROCYCLIC POLYIMINE INTERMEDIATES

(75) Inventors: Michael Leo Tulchinsky, Midland, MI (US); Barry B. Fish, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 603 days.

(21) Appl. No.: 11/922,687

(22) PCT Filed: Jun. 29, 2006

(86) PCT No.: PCT/US2006/025559
§ 371 (c)(1),
(2), (4) Date: Dec. 20, 2007

(87) PCT Pub. No.: WO2007/005594
PCT Pub. Date: Jan. 11, 2007

(65) Prior Publication Data
US 2010/0222611 A1    Sep. 2, 2010

Related U.S. Application Data

(60) Provisional application No. 60/695,489, filed on Jun. 30, 2005.

(51) Int. Cl.
*C07C 209/00*    (2006.01)
(52) U.S. Cl.
USPC .......................................... 564/446; 564/445

(58) Field of Classification Search
None
See application file for complete search history.

(56) References Cited

U.S. PATENT DOCUMENTS

| | | |
|---|---|---|
| 2,894,038 A | 7/1959 | Bartlett |
| 5,041,675 A | 8/1991 | Lukas |
| 5,055,618 A | 10/1991 | Kampmann |
| 5,371,292 A | 12/1994 | Merger |
| 5,789,620 A | 8/1998 | Waldmann |
| 5,973,208 A | 10/1999 | Nagareda |
| 6,252,121 B1 | 6/2001 | Argyropoulos |
| 2004/0116692 A1* | 6/2004 | McManus et al. ............ 540/575 |
| 2008/0167499 A1* | 7/2008 | Molitor et al. ................ 564/446 |

FOREIGN PATENT DOCUMENTS

JP    10-130210    5/1998

OTHER PUBLICATIONS

Kusaka et al., "Characterization of unsupported Ru-Co bimetallic catalyst derived from CoCo3 . . . ", Applied Catalysis A: General 185 (1999) 227-235.

* cited by examiner

*Primary Examiner* — Clinton Brooks
(74) *Attorney, Agent, or Firm* — Gary C Cohn PLLC

(57) ABSTRACT

Aldehyde or ketone compounds having more than one carbonyl group are reductively aminated to form a product amine compound having more than one primary amino group. The aldehyde or ketone compound is reacted with the product amine compound, to form a reaction mixture that contains one or more intermediates. The intermediate is then reductively aminated to form the desired product. This process produces the desired product in very high yields with low levels of secondary amine impurities.

4 Claims, No Drawings

PROCESS FOR THE REDUCTIVE AMINATION OF ALDEHYDES AND KETONES VIA THE FORMATION OF MACROCYCLIC POLYIMINE INTERMEDIATES

This application claims benefit of U.S. Provisional Patent Application 60/695,489, filed 30 Jun. 2005.

The invention relates to a method for preparing diamines via a reductive amination process.

Bis(aminomethyl)cyclohexane is a diamine that has applications as a precursor to an aliphatic diisocyanate (bis(isocyanatomethyl)cyclohexane). It is useful as a chain extender in certain polyurethanes systems and can be used as an epoxy curing agent. Bis(aminomethyl)cyclohexane exists as a number of isomers, of which the 1,3- and 1,4-isomers are of primary interest. The 1,3- and 1,4-isomers can also exist in a number of diastereomeric forms, as the aminomethyl groups can each reside above or below the plane of the cyclohexane ring.

1,3- and 1,4-bis(aminomethyl)cyclohexane mixtures can be prepared via a number of synthetic routes. A route of interest starts with butadiene and acrolein, which forms 1,2,3,6-tetrahydrobenzaldehyde in a Diels-Alder reaction. This intermediate is then hydroformylated to add a second aldehyde group and reductively aminated to form the desired diamine. A mixture of isomeric forms of the diamine is obtained. See, e.g., U.S. Pat. No. 6,252,121.

The reductive amination of hydroformylated 1,2,3,6-tetrahydrobenzaldehyde using a Raney metal catalyst or nickel on silica gellalumina as in U.S. Pat. No. 6,252,121, tends to produce the desired diamine product in low yields. A significant portion of the starting material forms unwanted by-products and polymeric species. As a result, raw material costs are high and purification of the crude product can be difficult and expensive. Polymeric by-products often foul the reactor.

It is sometimes possible to suppress by-product formation in reductive amination reactions by "protecting" (or "blocking") the aldehyde groups with an alkyl amine. See, e.g., U.S. Pat. Nos. 5,041,675 and 5,055,618. The blocked groups are more resistant to polymerization and other unwanted side reactions. However, this approach requires the use of additional raw materials and introduces additional chemical species into the reaction, which must later be removed from the crude product and recycled. Process yields are still far short of those that are needed to have a highly economical process.

It would be desirable to provide a method by which cycloaliphatic bis(aminomethyl) compounds can be prepared economically and in high yield.

This invention is in one respect a method for reductively aminating a starting aldehyde or ketone compound having at least two aldehyde or ketone groups per molecule to form a product amine compound, comprising (a) mixing the starting aldehyde or ketone compound with a quantity of the product amine compound to form a liquid mixture, and (b) subjecting the liquid mixture to reductive amination conditions in the presence of ammonia and hydrogen to produce additional product amine compound, wherein during steps a) and b) the molar ratio of product amine compound to starting aldehyde or ketone compound in the mixture is 1:1 or greater.

This invention is also a method for reductively aminating a starting aldehyde or ketone compound having at least two aldehyde or ketone groups per molecule to form a product amine compound, comprising a) mixing product amine compound and the starting aldehyde or ketone compound at a molar ratio of at least about 1:1 to form a reaction mixture, and maintaining said liquid mixture under non-reductive amination conditions sufficient to form an intermediate mixture containing reaction intermediates formed from the product amine compound and the starting aldehyde or ketone compound, which reaction intermediates consist mainly of one or more macrocyclic polyimine compounds; and b) thereafter subjecting the reaction intermediates to reductive amination conditions in the presence of ammonia and hydrogen to convert the macrocyclic polyimine compound to the product amine compound.

This invention is also a method for reductively aminating a starting aldehyde or ketone compound having two or more aldehyde or ketone groups to form a product amine compound, comprising a) mixing product amine compound and the starting aldehyde or ketone compound at a molar ratio of at least about 1:1 to form a liquid mixture, and maintaining said liquid mixture at a temperature of about 0 to about 50° C. for a period of at least 5 minutes to form an intermediate mixture; and b) thereafter subjecting the intermediate mixture to reductive amination conditions in the presence of ammonia and hydrogen to form the product amine compound.

This invention is also a method for reductively aminating an alicyclic dialdehyde or alicyclic diketone compound in which the carbonyl carbons of the aldehyde or ketone groups are attached directly to an alicyclic ring structure, to form a product alicyclic diamine compound, comprising a) mixing product alicyclic diamine compound and the starting alicyclic aldehyde or alicyclic ketone compound at a molar ratio of at least about 1:1 to form a liquid mixture, and maintaining said solution at a temperature of about 0 to about 50° C. for a period of at least 5 minutes to form an intermediate mixture; and b) thereafter subjecting the intermediate mixture to reductive amination conditions in the presence of ammonia and hydrogen to form the product alicyclic diamine compound.

This invention is also a continuous or semi-continuous method for reductively aminating a starting aldehyde or ketone compound having at least two aldehyde or ketone groups per molecule to form a product amine compound, comprising continuously or intermittently feeding the starting aldehyde or ketone compound to a reaction zone which is maintained at reductive amination conditions and contains product amine compound, ammonia and hydrogen, wherein the starting aldehyde or ketone compound is fed into the reaction zone at a rate such that the molar ratio of product amine compound to starting aldehyde compound in the reaction zone is maintained at 1:1 or higher.

This process permits the product polyamine compound to be produced in very high yields, typically at least 70%, at least 80%, at least 90% or even higher, based on the starting aldehyde or ketone compound. Surprisingly, the mixture of product amine with the starting aldehyde or ketone compound does not polymerize to form a high molecular weight polymer. Instead, it is believed that low molecular weight intermediate species form that remain soluble in the reaction mixture and are readily converted to form more of the product polyamine under reductive amination conditions. In embodiments of the invention described below as the two-stage process, it is believed that macrocyclic species mostly having molecular weights of about 450 or less to about 1500 tend to form, together with some linear reaction products of similar molecular weight. A further advantage of this process is that somewhat high concentrations of reactants can be used. This reduces or eliminates the requirement for solvents and in that manner reduces the volume of material that must be handled.

The smaller process volumes reduce the size and therefore the cost of the equipment that is needed to operate the process. The ability to use somewhat high concentrations of starting materials is considered to be quite surprising, as macrocyclic compounds are usually formed only under high dilution conditions (see, for example, H. An, J. S. Bradshaw, R. M. Izatt, Chem. Rev. 1992, 92, 543-572), while high starting material concentrations usually favor the production of high molecular weight, insoluble polymers that are difficult or impossible to reductively aminate.

The process has high selectivity to the desired primary amine products. In particular, unwanted secondary macrocyclic amine compounds are not formed in significant quantities.

The method of the invention is applicable to making a variety of amine compounds from the corresponding starting aldehyde or ketone compound. The aldehyde or ketone starting material has two or more aldehyde or ketone groups per molecule. It preferably contains 2 or 3, most preferably 2, such groups/molecule. The starting aldehyde or ketone compound for use in a two-stage process as described below preferably is one which is capable of reacting with the product amine compound to form mainly macrocyclic polyimine compounds. Macrocyclic polyimine formation is favored when (a) the aldehyde or ketone groups are equivalent and (b) when the aldehyde or ketone compound contains a somewhat rigid and/or bulky structure that constrains the spatial relationship between the aldehyde or ketone groups.

Aldehyde or ketone groups are considered to be equivalent for purposes of this invention if the carbon atoms to which the respective carbonyl carbons are attached, plus the adjacent carbon atoms, are identically substituted (or unsubstituted, as the case may be) in each instance. In the case of dialdehydes and diketones, it is preferred that the molecule is symmetrical about at least one line of symmetry between the carbonyl carbons.

Examples of rigid and/or bulky structures include cycloaliphatic moieties, which can be monocyclic, bicyclic or polycyclic. The cycloaliphatic moiety preferably contains at least one aliphatic ring structure that contains from 4 to 8 atoms in a ring (although it may also contain other ring structures as well). The carbonyl carbons of the aldehyde or ketone groups are preferably attached directly to a carbon atom of the ring structure. The ring structure may contain one or more heteroatoms provided that the ring structure is inert to the conditions of the process. Preferred ring structures include cyclohexane, cyclopentane, cycloheptane and cyclooctane. Such moieties are preferably substituted with the aldehyde or ketone groups in the 1,3- or 1,4-positions (or 1,5-positions in the case of cyclooctane).

Specific aldehyde and ketone compounds that are useful in this invention include 1,3-cyclopentanedicarboxaldehyde, 1,3- and 1,4-cyclohexanedicarboxaldehyde, 1,3- and 1,4-cycloheptanedicarboxaldehyde, 1,3-, 1,4-, and 1,5-cyclooctanedicarboxaldehyde, tetrahydro-2H-pyran-3,5-dicarbaldehyde, tetrahydro-2H-pyran-2,5-dicarbaldehyde, 1-methylpiperidine-3,5-dicarbaldehyde, 1-methylpiperidine-2,5-dicarbaldehyde, tetrahydro-2H-thiopyrane-3,5-dicarbaldehyde, tetrahydro-2H-thiopyran-2,5-dicarbaldehyde, 1,3-diacetylcyclopentane, 1,3- and 1,4-diacetylcyclohexane, 1,3- and 1,4-diacetylcycloheptane, 1,3-, 1,4- and 1,5-diacetylcyclooctane. Corresponding product amine compounds include 1,3-bis(aminomethyl)cyclopentane, 1,3- and 1,4-bis (aminomethyl)cyclohexane, 1,3- and 1,4-bis(aminomethyl) cycloheptane, 1,3-, 1,4-, and 1,5-bis(aminomethyl)cyclooctane, 3,5-bis(aminomethyl)tetrahydro-2H-pyran, 2,5-bis (aminomethyl)tetrahydro-2H-pyran, 3,5-bis(aminomethyl)-1-methylpiperidine, 2,5-bis(aminomethyl)-1-methylpiperidine, 3,5-bis(aminomethyl)tetrahydro-2H-thiopyran, 2,5-bis(aminomethyl)tetrahydro-2H-thiopyran, 1,3-bis(1-aminoethyl)cyclopentane, 1,3- and 1,4-bis(1-aminoethyl)cyclohexane, 1,3- and 1,4-bis(1-aminoethyl)cycloheptane, 1,3-, 1,4-, and 1,5-bis(1-aminoethyl)cyclooctane.

The product amine compound contains primary amino groups at the sites of the aldehyde or ketone groups of the starting material.

The process of the invention is conducted such that the reductive amination reaction is performed on a reaction mixture that contains product amine and starting aldehyde or ketone compound at a molar ratio of at least 1:1. Under these conditions, the starting aldehyde or ketone compound rapidly forms low molecular weight intermediates which are then reductively aminated to form more of the product amine.

In some embodiments of the invention, the mixture of product amine and starting aldehyde or ketone compound is formed under reactive amination conditions. Reductive amination conditions typically include (1) the presence of ammonia and hydrogen, (2) superatmospheric pressures, (3) elevated temperatures and (4) the presence of an active hydrogenation catalyst. Embodiments in which the product amine and starting aldehyde or ketone compound are brought together under reductive amination conditions are sometimes referred to herein by the shorthand term "single-stage" processes.

In other embodiments, product amine and starting aldehyde or ketone compound are mixed together under non-reductive amination conditions. Non-reductive amination conditions are those at which no significant reductive amination of the starting aldehyde or ketone compound (or intermediates) occurs. Non-reductive amination conditions include any set of conditions that lack at least one condition that is necessary for the reductive amination to occur. The missing condition may be, for example, the absence of hydrogen or ammonia, the lack of a hydrogenation catalyst, or the lack of sufficient temperature and/or pressure conditions. Two or more of these conditions may be lacking. Processes in which the product amine and starting aldehyde or ketone compound are brought together under non-reductive amination conditions are sometimes referred to herein by the shorthand "two-stage" processes. In the two-stage process, it is generally preferable to conduct the first reaction stage in the absence of the hydrogenation catalyst, at a temperature lower than that required for the reductive amination reaction to significantly occur, or both.

The single-stage process is conveniently conducted by forming a mixture of the product amine, ammonia and hydrogen, and heating the mixture to a temperature sufficient for the reductive amination reaction to proceed. This mixture is then contacted with starting aldehyde or ketone product, preferably in the presence of a reaction catalyst as described below. The starting aldehyde or ketone compound is added to the reaction mixture at such a rate that the molar ratio of product amine to starting aldehyde or ketone compound in the reaction mixture remains no higher than 1:1. Under the elevated temperatures generally required for the reductive amination to proceed, the product amine and starting aldehyde or ketone compound generally react very rapidly to form intermediates that then react to form more of the product amine. For this reason, instantaneous concentrations of starting aldehyde or ketone compound in the reaction mixture tend to remain small. Similarly, the molar ratio of product amine to starting aldehyde or ketone compound tends to be far in excess of 1:1 in the single-stage process. It is preferred that the concentration of starting aldehyde or ketone compound in the reaction mixture of a single-stage process is no higher than 35% by weight of the liquid components of the reaction mixture (i.e., product amine, starting aldehyde or ketone compound, intermediates, ammonia and any solvent that may be present). Typically, the concentration of starting aldehyde or ketone compound will be lower than 10% by weight, and more typically no more than 5% by weight, due to their rapid conversion of the starting material.

The single-stage process is optionally conducted with the starting aldehyde or ketone compound and product amine compound dissolved in a solvent. However, a solvent (other than ammonia, which can act as a solvent in the process) is not necessary in the single-stage process and is preferably omitted. A suitable solvent is one in which the starting materials are soluble in the proportions that are present in the reaction mixture. The solvent should not be reactive with those materials, or with ammonia or hydrogen, under the conditions of the process. The solvent should not interfere undesirably with the activity of any catalyst that is used for the reductive amination reaction. The solvent should remain a liquid under the conditions of the reductive amination process. Examples of solvents that can be used include methanol, ethanol and other aliphatic alcohols; toluene, xylene, tetrahydrofuran, dioxane, diglyme, dimethoxyethane, diethyl ether, and the like. Mixtures of two or more of the foregoing, as well as mixtures of one or more of the foregoing with water, are also useful. Methanol is a preferred solvent, as higher yields and selectivities are sometimes seen when methanol is used as the solvent. Ammonia can also act as a solvent in the process.

Superatmospheric pressures are used mainly to supply ample hydrogen to the reaction and to maintain ammonia and solvent in liquid form during the reaction. Hydrogen is typically provided to a partial pressure of at least 100 psig (689 kPa), preferably at least 200 psig (1379 kPa) and more preferably at least 300 psig (2068 kPa), up to 2000 psig (13,790 kPa), preferably up to about 1200 psig (8274 kPa) (all pressures as measured under reaction conditions). The upper limit on hydrogen pressure is mainly a matter of equipment design; however, little additional benefit is seen by increasing the hydrogen partial pressure above the stated ranges.

Suitable reaction temperatures are in the range of about 40-200° C., with a preferred temperature range being from 80-160° C. and a more preferred temperature range being from 120-150° C.

Anhydrous ammonia is preferably used as the ammonia source, although other sources of ammonia can be used as well. Ammonia is typically used in excess of the stoichiometric amount, it being preferred to use at least two moles of ammonia per equivalent of aldehyde groups provided by the starting aldehyde or ketone compound. The amount of ammonia may be as high as 100 moles or more per equivalent of aldehyde or ketone groups provided by the starting aldehyde or ketone compound. A preferred range is from 5-60 moles of ammonia per equivalent of aldehyde or ketone groups provided by the starting aldehyde or ketone compound.

A hydrogenation catalyst is present in order to provide a commercially reasonable reaction rate. A wide variety of such catalysts are known, including those described in U.S. Pat. No. 5,055,618 and U.S. Pat. No. 5,041,675. Suitable catalysts are transition metal catalysts, of which the nickel, copper and cobalt catalysts are of particular interest. Nickel catalysts are most preferred on the basis of good activity and selectivity and minimal metal leaching. The catalyst can be an unsupported catalyst such as a Raney nickel or Raney copper catalyst. Supported catalysts can be used as well. Specific examples of suitable catalysts include Raney 2724 (a nickel- and chromium-promoted copper catalyst available from Grace Davison) and especially catalysts Ni-5256 and Ni 0750, both available from Engelhard.

It may be necessary to activate the catalyst prior to the reaction. This is particularly true for non-Raney types of catalysts. Non-Raney catalysts can be activated by heating to a temperature of 100-250° C. in the presence of hydrogen for a period of 0.5 to 5 hours. The catalyst may be slurried in a solvent or diluent during this activation step.

Reaction times will of course depend on factors such as temperature, hydrogen partial pressure, and type and amount of catalyst. In general, though, a reaction time of from about 1.5 to about 20 hours is sufficient.

It is believed that in the single-stage process, the product amine compound and the starting aldehyde or ketone compound first react to form relatively low molecular weight intermediates. Because the product amine compound is present in excess (usually in large excess), it is believed that the predominant intermediate that is formed is the reaction product of two molecules of the product amine and one molecule of the starting aldehyde or ketone compound. Most probably, a mixture of intermediates are formed, which represent the reaction products of various ratios of product amine and starting aldehyde or ketone compound.

The single stage process lends itself readily to continuous or semi-continuous operation. During continuous or semi-continuous operation, the starting aldehyde or ketone compound is added continuously or intermittently to a reaction zone where product amine resides and reductive amination conditions have been established. Other starting materials can be introduced to the reaction zone batch-wise, intermittently or continuously. Hydrogen is conveniently supplied by pressurizing the reaction zone with hydrogen or a hydrogen-containing mixture of gases and feeding hydrogen on demand. Product may be withdrawn continuously or intermittently if desired, or allowed to accumulate in the reaction mixture.

In the first stage of a two-stage process, the starting aldehyde or ketone compound is combined with the product amine compound under non-reductive amination conditions to form an intermediate mixture that contains as a primary reaction product, one or more macrocyclic polyimines. In the second stage, the intermediate mixture, or at least a macrocyclic polyimine from the intermediate mixture, is reductively aminated to form the product amine compound.

In the two-stage process, the starting aldehyde or ketone compound is suitably added to the reaction mixture in an amount from about 10 to about 35% by weight, based on the combined weight of the starting aldehyde or ketone compound, product polyamine and solvent (if any) that are present at the start of the first reaction step. A preferred level of aldehyde or ketone compound is from about 10 to 30% by weight, and a more preferred level is from about 10 to 25% by weight. A significant advantage of the invention is that somewhat high concentrations of reactants as described can be present in the starting solution without significant formation of unwanted high molecular weight polymers or other unwanted reaction by-products. However, greater yield losses are sometimes seen in a two-stage process when higher concentrations of starting materials are used.

In the two-stage process, the product amine is suitably added to the first-stage reaction mixture in at least an equimolar amount, based on the amount of starting aldehyde or ketone compound. A small molar excess of the product polyamine, such as a 5-50% excess or especially a 10-30% molar excess, is preferable, as this tends to drive the first step reaction towards the generation of the desired macrocyclic polyimine intermediate material. Generally, an excess of greater than about 50 mole-% tends to result in yield losses in the two-stage process.

The product amine compound that is added into the first stage of a two-stage process may be a purified material, but preferably is a crude product of the reductive amination step, which is partially recycled back to the start of the process. Such a crude amine may include reaction by-products, solvent, ammonia or even small amounts of hydrogen.

It is highly preferred to conduct the two-stage process in the presence of a solvent. Suitable solvents are as described before, although ammonia typically is not used as a solvent for the first stage of a two-stage process. The solvent suitably constitutes from 5 to 90%, preferably from 10 to 50% by weight of the liquid components of the reaction mixture (i.e., product amine, intermediates, starting aldehyde or ketone compound and ammonia (if in liquid form)).

The first stage reaction of the starting aldehyde or ketone compound with the product polyamine in most cases proceeds under mild conditions. At atmospheric pressure and room temperature (~22° C.), for example, the reactants typically form reaction intermediates within a short period, such as an hour or less, typically about 30 minutes or less. The reaction period preferably is at least five minutes. Higher temperatures can be used to accelerate the reaction, but this is generally not necessary. If a higher temperature is used during the first reaction step, it is suitably in the range of from about 22 to 50° C., more preferably in the range of from about 22 to 40° C. As the reaction of the starting aldehyde or ketone compound and product amine is exothermic, it may be necessary to bring the components together slowly and/or apply cooling to avoid an undesired temperature spike. In the two-stage process, it is preferred to maintain any such temperature spike to below 50° C., and especially below 40° C. Temperatures somewhat lower than room temperature, such as from 0 to 22° C., can be used if desired, although reaction rates may be slower.

The first reaction stage can be conducted at atmospheric pressure, although higher pressures can be used if desired. Pressures greater than atmospheric may be useful when the reaction mixture contains volatile components (such as ammonia or a solvent such as methanol), in order to prevent those materials from flashing.

Because the hydrogenation reaction can be prevented during the first reaction stage through control of temperature and/or the absence of catalyst, it is possible that ammonia and/or hydrogen can be present during that stage. This makes it possible to use a crude product amine compound (rather than a purified stream) in the first reaction stage.

The formation of intermediates in the first reaction stage of a two-stage process can be detected and followed using analytical methods such as electrospray ionization mass spectroscopy and/or gel permeation chromatography. Alternatively, conditions sufficient to obtain the desired conversion to the intermediates can be established empirically.

The intermediate formed during the first stage of the reaction is believed to consist mainly (i.e., at least 50% by weight, especially 70-99% by weight) of macrocyclic polyimine species. A "macrocyclic" polyimine species is a cyclic reaction product of at least two moles of the starting aldehyde or ketone compound with an equal number of moles of the product amine. The macrocyclic polyimine will typically include a mixture of cyclic compounds mainly having molecular weights of about 450 to about 1500.

For example, in the case of a cyclohexanedicarboxaldehyde amination, a ~494 molecular weight species is produced that corresponds to a cyclic reaction product of two moles of the starting cyclohexanedicarboxaldehyde with two moles of the product diamine (A2B2 species, where A represents the starting dicarboxaldehyde and B represents the starting diamine). This macrocyclic intermediate can be represented by the following structure I:

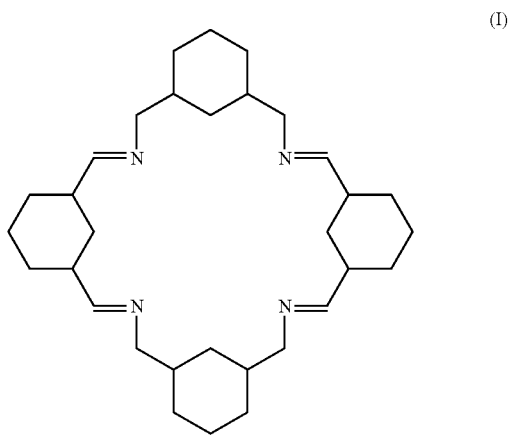 [SMILES: C1=N/CC2CCCC(C/N=C/C3CCCC(/C=N/CC4CCCC(C/N=C/C5CCCC/1C5)C4)C3)C2]

(I)

The ~494 molecular weight product tends to be the most prevalent species. In addition, species corresponding to the cyclic A3B3, A4B4 and A5B5 species are typically present. A ~1480 molecular weight product is also produced, which corresponds to the cyclic reaction product of six moles of the starting cyclohexanedicarboxaldehyde with six moles of the product diamine (A6B6 species). There are also produced a series of linear species having molecular weights mainly up to about 1500, mostly up to about 1000. The use of a slight excess of the product diamine tends to favor the production of a minor amount of these linear species. Such linear species preferably constitute no more than about 20% by weight of the reaction products in the two-stage process. Linear species more preferably constitute no more than about 10% and most preferably no more than 5% of the weight of the reaction intermediates.

It is believed that such macrocyclic species may also form in some quantities in the one-stage process described before, but that they are rapidly reductively aminated in the one-stage process to form the product amine, and so the macrocyclic species may not accumulate to significant concentrations in the one-stage process.

It is not necessary to recover the intermediate mixture from the solvent or otherwise purify it prior to conducting the amination/hydrogenation reaction in the two-stage process. It is possible to conduct both reaction stages in a single vessel, by conducting the first reaction stage in the presence of the catalyst, and then pressurizing the reaction vessel with ammonia and hydrogen and/or increasing the temperature until the amination/reduction reactions occur. The reactions can be run continuously in a tubular reactor or other suitable apparatus.

The two-stage process can be conducted batch-wise, in a semi-batch operation, or continuously.

A suitable arrangement for a continuous two-stage process includes at least two reactors arranged in series, the first reactor being for the intermediate-forming reaction and the second being for the reductive amination reaction. Starting aldehyde or ketone compound, recycled product amine compound and fresh or recycled solvent as needed is introduced into the entrance of the first reactor. The first reactor is maintained at non-reductive amination conditions described before. The reaction mixture exits the first reactor (after the required residence time) and introduced into the second reactor, together with ammonia and hydrogen feeds. The second reactor contains the catalyst and is operated at reductive amination conditions as described before. Product exiting the second reaction is separated from most or all of the unreacted hydrogen, which is preferably recycled into the second reactor. The remaining product stream is separated into an ammonia recycle stream (which is recycled to the second reactor), a byproduct stream (which is sent to disposal or elsewhere), and a product stream. The product stream is divided between a recycle stream, which is fed back into the first reactor, and final product which is sent to be purified or to downstream operations (such as phosgenation, when the amine product is to be used as a raw material for polyisocyanate production). Alternately, the entire product stream may be purified, with a portion of the purified product recycled back to the start of the process.

The aminated and hydrogenated product (from either the one-stage or two-stage embodiments) contains the product amine compound, together with a small amount of reaction by-products. Yields to the desired amine product are typically over 70%, and preferably over 80% based on the starting aldehyde or ketone compound. Yields are often somewhat higher for the two-stage process than the one-stage process. Yields in a two-stage process are often over 90%. Yields of 93-98% are often achieved in two-stage process. In dialdehyde reductive amination reactions, impurities often include one or more bicyclic imine compounds (such as 3-azabicyclo[3.3.1]-2-nonene), and/or bicyclic diamine compounds (such as 2-amino-3-azabicyclo[3.3.1]nonane), both of which are indicative of an incomplete reaction. The bicyclic imine compound can react with additional ammonia to generate the bicyclic diamine, which in turn can be hydrogenated to form the desired product amine compound. Bicyclic amine compounds such as 3-azabicyclo[3.3.1]nonane can also form. The bicyclic amine compounds cannot be easily converted to the desired product. A small amount of other by-products is also produced.

The product amine compound will in most cases exist as a mixture of isomers and, depending on the starting material, may also exist as a mixture of diastereoisomers. In the preferred case where the product is bis(aminomethyl)cyclohexane, the product is a mixture of the 1,3- and 1,4-isomers, each of which can exist in both cis- and trans-configurations. The amounts of the 1,3- and 1,4-isomers are approximately equal. A typically desirable bis(aminomethyl)cyclohexane product mixture includes 45-60% of the 1,3-isomer, and 40-55% of the 1,4-isomer.

The crude product of the reductive amination reaction includes the product amine compound, a small quantity of by-products, unreacted ammonia and hydrogen, and solvent. The product is readily recovered using any convenient methods. Ammonia, hydrogen and solvent can be stripped from the product by venting, applying vacuum and/or applying an elevated temperature.

The product amine compound is useful as an intermediate in the synthesis of various downstream products. It can be used as a chain extender or crosslinker for polyurethanes and as an epoxy curing agent. An application of particular interest is the manufacture of diisocyanate compounds, which are conveniently formed in the reaction of the amine groups with phosgene. Conditions for conducting such phosgenation reactions are well-known and described, for example, in U.S. Pat. Nos. 4,092,343, 4,879,408 and 5,516,935. The diisocyanate compounds are useful in making a wide variety of polyurethane and polyurea polymers.

The following examples are provided to illustrate the invention, but are not intended to limit the scope thereof. All parts and percentages are by weight unless otherwise indicated.

EXAMPLE 1

A mixture of 1,3- and 1,4-cyclohexanedicarboxaldehyde (3.08 g, 22 mmol) and a mixture of 1,3- and 1,4-bis(aminomethyl)cyclohexane (4.26 g, 30 mmol) are dissolved in 11 g of methanol. Diglyme (2.38 g) is added as an internal standard for gas chromatographic analysis. The mixture is stirred at room temperature for 30 minutes. During this time, the reactants form an intermediate product mixture containing mostly macrocyclic polyimine species of about 490 to 1480 molecular weight.

A powdered nickel catalyst (Ni-5256W from Engelhard) (0.75 g) is placed in a 160 mL Parr reactor together with 30 g methanol. The reactor is purged with 100 psi (689 kPa) nitrogen three times, charged with 1000 psi (6895 kPa) hydrogen and heated to 200° C. for two hours to activate the catalyst. The reactor is then cooled and the hydrogen vented off. The intermediate product mixture from above is then transferred into the reactor. Anhydrous ammonia (37.7 g, 2.22 mol) is added with stirring under reduced temperature. The reactor is sealed and pressurized to 300 psi (2068 kPa) with hydrogen. The reactor is then heated to 130° C. with stirring and the hydrogen pressure adjusted to 1000 psi (6895 kPa). These conditions are maintained for five hours, and the reaction contents are recovered. Yield to 1,3- and 1,4-bis(aminomethyl)cyclohexane is 97% by gas chromatography. Isomer ratios are 54.5% of the 1,3-isomer and 45.5% of the 1,4-isomer.

EXAMPLE 2

Example 1 is repeated without addition of the diglyme. After the reductive amination is completed, the catalyst is filtered from the reaction mixture and washed twice with methanol (50 g). The wash liquid is combined with the reaction mixture. The methanol is then evaporated off, followed by flash distillation in vacuum at 70-75° C./1 mm Hg to provide 6.61 g of 1,3- and 1,4-bis(aminomethyl)cyclohexane (91% isolated yield).

EXAMPLE 3

Example 1 is repeated, except the temperature during the hydrogenation step is only 120° C., the reaction time is 3 hours, and the ratio of ammonia to aldehyde groups provided by the starting mixture of 1,3- and 1,4-cyclohexanedicarboxaldehyde is 25. Yield to 1,3- and 1,4-bis(aminomethyl)cyclohexane is 88%. About 9% 3-azabicyclo[3.3.1]nonane is formed. The presence of the latter species indicates that the amination/reduction reaction has not been completed in the given time at the 120° C. temperature and the amount of ammonia that is used.

EXAMPLE 4

Example 1 is again repeated, this time reducing the amount of solvent so that the concentration of starting 1,3- and 1,4-cyclohexanedicarboxaldehyde is approximately doubled. The amount of ammonia is decreased so the ratio of moles of ammonia to equivalents of aldehyde groups provided by starting aldehyde is reduced from 50.4 (in Example 1) to about 25. Yield to 1,3- and 1,4-bis(aminomethyl)cyclohexane is 94%.

5% of 3-azabicyclo[3.3.1]nonane is formed. Isomer ratios are 54.6% of the 1,3-isomer and 45.4% of the 1,4-isomer.

EXAMPLE 5

Example 1 is repeated again, reducing the amount of methanol so the starting dicarboxaldehyde concentration is approximately triple that used in Example 1. The ammonia/aldehyde group ratio is reduced to about 12.5. Yield to 1,3- and 1,4-bis(aminomethyl)cyclohexane is 93%. Isomer ratios are 55.1% of the 1,3-isomer and 44.9% of the 1,4-isomer.

EXAMPLE 6

Example 1 is again repeated, this time reducing the amount of methanol so the starting dicarboxaldehyde concentration is approximately five times that used in Example 1. The ammonia/aldehyde group ratio is reduced to about 6.4. Yield to 1,3- and 1,4-bis(aminomethyl)cyclohexane is 93%. Isomer ratios are 52.9% of the 1,3-isomer and 47.1% of the 1,4 isomer.

EXAMPLES 7-9

A powdered Raney nickel catalyst (Ni5256, from Engelhard, 25 g) is ground and added to a 1-gallon autoclave. The reactor is purged with 100 psi (689 kPa) nitrogen three times and 100 g methanol is added. The reactor is then charged with hydrogen, heated to 190° C., and the pressure increased to 1000 psi (6895 kPa) with more hydrogen. The reactor contents are held at these conditions for 2 hours to activate the catalyst. The reactor is then cooled and the hydrogen vented off.

477 grams of a refined bis(aminomethyl)cyclohexane are charged to the reactor followed by 200 grams of methanol. A crude (85% purity) mixture of 1,3- and 1,4-cyclohexanedicarboxaldehyde) (425 g) is then added slowly with cooling to maintain the temperature of the reaction contents below 40° C. 100 g of additional methanol are added to rinse feed lines. The solution is then stirred for 30 minutes. 900 g of anhydrous ammonia are added and the reactor is pressurized to 300 psi (2068 kPa) with hydrogen. The reactor is then heated to 130° C. and pressurized to 1000 psi (6895 kPa) with hydrogen. These conditions are maintained for 17 hours, after which the reactor is vented and cooled. The product (Example 7) is collected and analyzed by gas chromatography. Results are as indicated in Table 2 below.

Example 8 is conducted in a similar manner, except that a crude diamine containing about 60% by weight of the diamine and 20% by weight of methanol is used instead of the refined material used in Example 7. The diamine is the crude product of a reductive amination similar to Example 7, from which ammonia and hydrogen have been removed. Amination/hydrogenation conditions are maintained for 19.5 hours. Results are as indicated in Table 2 below.

Example 9 is conducted in a manner similar to Example 7, except a crude diamine from a reductive amination similar to Example 7 is used. Hydrogen but not ammonia is removed from the crude diamine. Amination/hydrogenation time is 15 hours. Results are as indicated in Table 2.

Table 1 summarizes the amounts of starting materials used in each of Examples 7-9:

TABLE 1

| | Amount (g) Example No. | | |
|---|---|---|---|
| | 7 | 8 | 9 |
| Added methanol | 400 | 261 | 271 |
| Diamine* | 477 | 708 | 725 |
| Crude dialdehyde (85%) | 425 | 425 | 429 |
| Ammonia | 900 | 800 | 865 |
| Catalyst | 25 | 25 | 25 |
| Hydrogen | 1000 psi (6895 kPa) | 1000 psi (6895 kPa) | 1000 psi (6895 kPa) |

*Refined diamine in Example 7; crude diamines in Examples 8 and 9 that contain about 60% by weight of the diamine and 20% by weight of methanol; the crude diamine used in Example 10 also contains ammonia.

Table 2 summarizes the yield, selectivity and isomer distribution of the products of Examples 7-9. For comparison, the isomer distributions of the starting dialdehyde, refined diamine reactant and crude diamine reactant are provided.

TABLE 2

| | | Isomer Distribution | |
|---|---|---|---|
| Example No. | Selectivity | % 1,3 isomer | % 1,4 isomer |
| 7 | 95 | 54.8 | 45.2 |
| 8 | 90 | 48.6 | 51.4 |
| 9 | 98 | 53.5 | 46.3 |
| Refined Diamine | — | 55.8 | 44.2 |
| Crude Diamine | — | 52.5 | 47.5 |
| Starting dialdehyde | — | 53.3 | 46.7 |

Little change in results is obtained with the variation in diamine feedstock, indicating that a crude diamine reaction product will work well when recycled into the start of the process.

Comparative Run A

A mixture of 1,3- and 1,4-cyclohexanedicarboxaldehydes (1.017 g; 7.42 mmol), diglyme (0.4033 g, as an internal standard), a Ni catalyst supported on silica/alumina (0.2 g), and methanol (25 ml) are sealed in an 80 ml Parr reactor. Ammonia (6.5 g; 382 mmol) is transferred into the autoclave at ambient temperature. The reactor is heated to 100° C. over a 10-15 minute period and kept at that temperature for 30 minutes. Gas chromatography analysis shows complete consumption of the aldehyde. Then 800 psi (5516 kPa) of hydrogen is charged, and the reaction was continued at 100° C. at constant hydrogen pressure. After 5 hours, the yields to diamines (1,3- and 1,4-bis(aminomethyl)cyclohexane) and 3-azabicyclo[3.3.1]nonane are 52% and 27%, respectively.

EXAMPLE 10

A mixture of 1,3- and 1,4-bis(aminemethyl)cyclohexane isomers is prepared in a semi-batch, one-step process. 10.0 g of cyclohexanedimethyldiamine and 2 g of Engelhard Ni-5256P catalyst are added to a 300 ml autoclave equipped with a stirrer. The reactor is closed and 61.8 g of anhydrous ammonia is added to the reactor while stirring. The reactor is then heated to 120° C. to produce a reactor pressure of 1272 psi (8770 kPa). The reactor pressure is increased by an additional 50 psi (345 kPa) by adding hydrogen. A feed burette is charged with a crude mixture of 1,3- and 1,4-cyclohexanedicarboxaldehyde, 86% purity. 53.75 g of the cyclohexanedicarboxaldehyde mixture is pumped into the reactor at a rate of 0.8 ml/min. The total time to pump in the feed is 73 minutes. The feed burette is then flushed with methanol to ensure that all of the cyclohexanedicarboxaldehyde has been fed into the reactor, without introducing a significant quantity of methanol into the reactor. Hydrogen is fed on demand during the cyclohexanedicarboxaldehyde addition, to maintain a constant internal reactor pressure. The reaction is continued after the cyclohexanedicarboxaldehdye addition for a total of about 5 hours. Hydrogen consumption stops after about 120 minutes of reaction time. The reactor is then cooled and vented, and the product is collected. The reactor is rinsed with methanol, and the rinse is collected.

46.2 g of the diamine is produced, for a molar yield of the dialdehyde to the diamine of 87%.

Comparative Run B

A 300 ml autoclave is charged with 2 g of Engelhard Ni-5256P catalyst and 57.6 g of the crude cyclohexanedicarboxaldehyde described in Example 10. The reactor is pressured with nitrogen and vented. 57 g of anhydrous ammonia are added to the reactor while stirring. The contents are heated to 100° C. to produce a reactor pressure of 760 psi (5240 kPa). Hydrogen is added to increase the pressure to 1058 psi (7295 kPa), and hydrogen is thereafter fed on demand to maintain this reactor pressure. The reaction is continued for 7 hours, until hydrogen uptake stops.

The total mass of diamine produced is 35 g, which represents a molar yield of the dialdehyde to the diamine of only 69%.

It will be appreciated that many modifications can be made to the invention as described herein without departing from the spirit of the invention, the scope of which is defined by the appended claims.

What is claimed is:

1. A method for reductively aminating 1,3-cyclohexanedicarboxaldehyde, 1,4-cyclohexanedicarboxaldehyde, or a mixture thereof to form 1,3-bis(aminomethyl)cyclohexane, 1,4-bis(aminomethyl)cyclohexane or a mixture thereof, comprising
   a) mixing 1,3-bis(aminomethyl)cyclohexane, 1,4-bis(aminomethyl)cyclohexane or a mixture thereof and 1,3-cyclohexanedicarboxaldehyde, 1,4-cyclohexanedicarboxaldehyde, or a mixture thereof at a molar ratio of at least about 1:1 but not greater than a 50% molar excess of the product amine to form a liquid mixture, and maintaining said liquid mixture at a temperature of about 0 to about 50° C. for a period of at least 5 minutes to form an intermediate mixture containing reaction intermediates wherein at at least 50% by weight of the reaction intermediates formed are macrocyclic polyimines having molecular weights of about 450 to about 1500;
   b) thereafter subjecting the intermediate mixture to reductive amination conditions in the presence of ammonia and hydrogen to form 1,3-bis(aminomethyl)cyclohexane, 1,4-bis(aminomethyl)cyclohexane or a mixture thereof.

2. The method of claim 1, wherein the concentration of 1,3-cyclohexanedicarboxaldehyde, 1,4-cyclohexanedicarboxaldehyde, or a mixture thereof in the liquid mixture is from 10 to 30% by weight, based on the combined weights of 1,3-cyclohexanedicarboxaldehyde, 1,4-cyclohexanedicarboxaldehyde, or a mixture thereof; 1,3-bis(aminomethyl)cyclohexane, 1,4-bis(aminomethyl)cyclohexane or a mixture thereof used in step a); and any solvent as may be present.

3. The method of claim 1 wherein the yield to 1,3-bis(aminomethyl)cyclohexane, 1,4-bis(aminomethyl)cyclohexane or a mixture thereof is at least 90%.

4. The method of claim 2 wherein the yield to 1,3-bis(aminomethyl)cyclohexane, 1,4-bis(aminomethyl)cyclohexane or a mixture thereof is at least 90%.

* * * * *